US007019654B2

(12) United States Patent  
Danyluk et al.

(10) Patent No.: US 7,019,654 B2
(45) Date of Patent: Mar. 28, 2006

(54) CONTACT POTENTIAL DIFFERENCE SENSOR TO MONITOR OIL PROPERTIES

(75) Inventors: Steven Danyluk, Atlanta, GA (US); Anatoly Zharin, Minsk (BY)

(73) Assignee: Georgia Tech Research Corporation, Atlanta, GA (US)

( * ) Notice: Subject to any disclaimer, the term of this patent is extended or adjusted under 35 U.S.C. 154(b) by 694 days.

(21) Appl. No.: 10/084,034

(22) Filed: Feb. 27, 2002

(65) Prior Publication Data

US 2002/0140564 A1 Oct. 3, 2002

Related U.S. Application Data

(60) Provisional application No. 60/279,596, filed on Mar. 29, 2001.

(51) Int. Cl.
 *G08B 21/00* (2006.01)
(52) U.S. Cl. .................... 340/603; 340/450.3
(58) Field of Classification Search ............ 340/603, 340/606, 450.3, 451, 632; 73/23.34
See application file for complete search history.

(56) References Cited

U.S. PATENT DOCUMENTS

| 4,646,070 A * | 2/1987 | Yasuhara et al. ............ 340/603 |
| 5,071,527 A * | 12/1991 | Kauffman .................... 205/786 |
| 5,136,247 A | 8/1992 | Hansen |
| 5,644,239 A * | 7/1997 | Huang et al. ................ 324/439 |
| 5,674,401 A * | 10/1997 | Dickert et al. .............. 210/695 |
| 5,754,055 A * | 5/1998 | McAdoo et al. ............ 324/636 |
| 5,824,889 A * | 10/1998 | Park et al. ..................... 73/116 |
| 6,278,281 B1 * | 8/2001 | Bauer et al. ................ 324/441 |
| 6,718,819 B1 * | 4/2004 | Schoess ...................... 73/53.05 |
| 6,774,645 B1 * | 8/2004 | Leidl et al. ................. 324/698 |

FOREIGN PATENT DOCUMENTS

DE          42 24 218          4/2001

OTHER PUBLICATIONS

Yano, D. et al., "Not Vibrating Contact Potential Difference Probe Measurement of Any Nanometer-Scale Lubricant on a Hard Disk", Journal of Tribology, American Society of Mechanical Engineers, New York, NY, US, vol. 121 No. 4, pp. 983-983.

* cited by examiner

*Primary Examiner*—Toan N. Pham
(74) *Attorney, Agent, or Firm*—Foley & Lardner LLP

(57) ABSTRACT

A method and system for contact potential sensing of dielectric properties of a fluid. The method and system include a contact potential sensor, an open or closed loop for passing a fluid past the sensor, measuring a contact potential to characterize dielectric properties of the fluid and outputting the dielectric property information for analysis and response thereto.

20 Claims, 3 Drawing Sheets

CONTACT POTENTIAL DIFFERENCE SENSOR TO MONITOR OIL PROPERTIES

This application claims the benefit of Provisional Application Ser. No. 60/279,596, filed Mar. 29, 2001.

This invention was made in part with U.S. Government support under a grant from the Office of Naval Research Contract No. N000140010374. The U.S. Government has certain rights in this invention.

FIELD OF THE INVENTION

The present invention is directed generally to a method and system for monitoring oil properties. More particularly the invention is directed to a method and system using a contact potential sensor to monitor properties of flowing oil

BACKGROUND OF THE INVENTION

A variety of mechanical systems, such as engines, require means to monitor the quality of oil used for lubrication and other functionalities. A number of prior art methods exist for performing this function, including, for example (1) an odometer monitor to time out the useful life of oil based on general lifetime assumptions, (2) a magnetic field sensor for sensing density of ferromagnetic particles in the oil, (3) a particle separating device to evaluate size and number of contaminating particles, (4) a threshold oil temperature sensor, (5) a corrodable sensor which undergoes electrical circuit break down as oil breaks down or suffers contamination, (6) a chemical prediction device to assess acid content in the oil, and (7) a light absorption sensor based on light attenuation by particles in the oil.

The above described prior art systems suffer from numerous disadvantages, such as, gross insensitivity to critical operating conditions to which oil is subjected, inability to be utilized in many applications due to structural size or geometry limitations, inability to sense other than ferromagnetic debris in the oil, and too specific a measure of oil degradation thereby ignoring many other indicators of oil condition.

SUMMARY OF THE INVENTION

It is therefore an object of the invention to provide an improved system and method for monitoring the condition of an oil.

It is yet another object of the invention to provide an improved contact potential sensor for monitoring the condition of oil flowing in a system.

It is a further object of the invention to provide an improved method and system for sensing the dielectric properties of oil.

It is an additional object of the invention to provide an improved method and system utilizing a non-vibrating contact potential difference probe to monitor the properties of flowing oil and other dielectric media.

It is also an object of the invention to provide an improved method and system for establishing an electric field probe for sensing the dielectric properties of oil.

It is in addition an object of the invention to provide an improved method and system to characterize a changing contact potential to assess the ongoing condition of an oil undergoing use.

It is yet a further object of the invention to provide an improved system and method for monitoring properties of a fluid flowing past a contact potential difference sensor.

It is also another object of the invention to provide an improved method and system for separating molecules in a flowing fluid to characterize the condition of the fluid.

It is still a further object of the invention to provide an improved method and system identifying signatures associated with selected constituents of an oil undergoing degradation from use.

It is yet an additional object of the invention to provide an improved method and system to evaluate rate of degradation of oil and other fluids undergoing use in a system.

It is also a further object of the invention to provide an improved system and method for characterizing flowing oil, and other fluids or gases having a changing dielectric condition.

Further advantages and features of the present invention will be apparent from the following description of the drawings, specifications and claims illustrating the preferred embodiments of the invention.

DETAILED DESCRIPTION OF THE PREFERRED EMBODIMENTS

Figure 1:
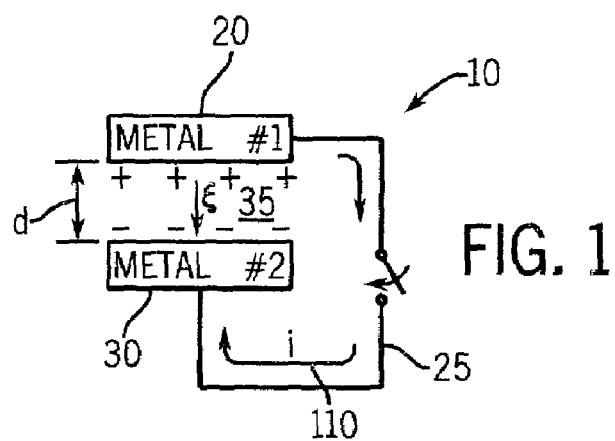
FIG. 1 illustrates a schematic of a contact potential difference sensor.

An illustration of the principals used to monitor properties of oils, other fluids and even particular gaseous environments is shown schematically in FIG. 1. A contact potential sensor 10 is illustrated wherein a first conductive material 20, such as a first metal, is electrically coupled by a connection 25 to a second conductive material 30, such as a second metal. In particular the sensor 10 is a non-vibrating contact potential difference probe. An electric field, $\vec{\in}$, arises between the first conductive material 20 and the second conductive material 30 when the two materials are electrically connected, and the electric field, $\vec{\in}$, will form when the Fermi energies of the two materials 20 and 30 are equilibrated. The strength of the electric field, $\vec{\in}$, will depend on the dielectric properties, a relative dielectric constant, $\in_r$, of the material disposed in gap 35 between the two materials 20 and 30. In general, the sensor 10 can operate to sense dielectric properties of fluids, such as oil, and even dense gases flowing past the sensor 10.

Figure 2:
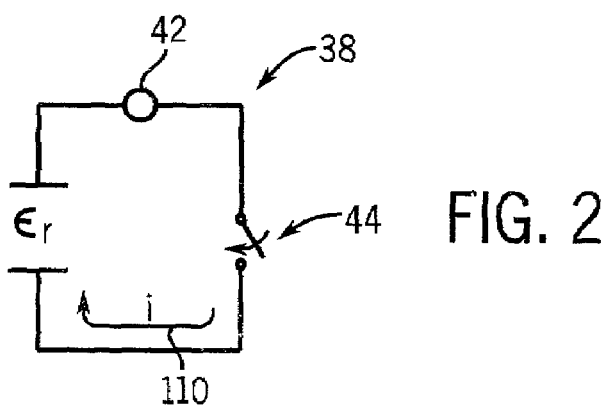
FIG. 2 illustrates one form of electrical circuit for the sensor of FIG. 1.

The first and second conductive materials 20 and 30 when electrically connected compose an electrochemical cell, and an electrical current 110 will result if oil 46 and/or one of its constituents disposed between the materials 20 and 30 conducts electrical charge. As the oil 46 flows past the two surfaces of the materials 20 and 30, the electrical field, ∈, separates the charges of the oil 46, the positive charges tending toward the negative surface and vise versa. The current density will depend on the interfacial electron transfer reactions of the oil 46, and its constituents on the temperature and on the contact potential difference between the materials 20 and 30. The current density can be written as:

$$i = K_1 T \in K_2 \in /kT$$

where i is the current density (amperes/cm²), $K_1$ is a constant, T is the temperature, $K_2$ is another constant, ∈ is the electrical field produced by the contact potential difference, and k is Boltzmann's constant. It can also be written that v, the number of ions per unit time striking the electrodes is:

$$V = i/F$$

where F is the Faraday's constant, and i is the current in circuit 38 having a circuit component 42, such as an alarm indicator, display or the like and also can include a switch 44 (see FIG. 2).

Figure 3:
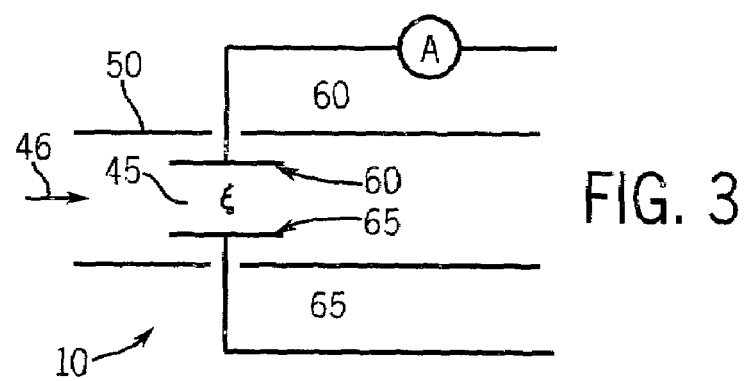
FIG. 3 illustrates a system with a flow of oil past the contact potential difference sensor of FIG. 1.
Figure 4:
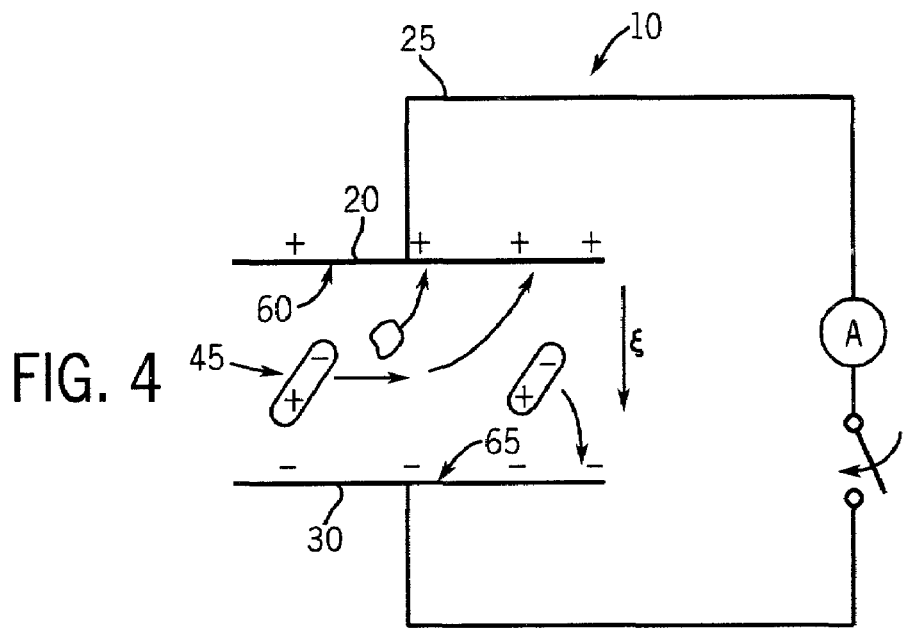
FIG. 4 illustrates schematically the separation of molecular components of oil in the system of FIG. 2.
Figure 5:
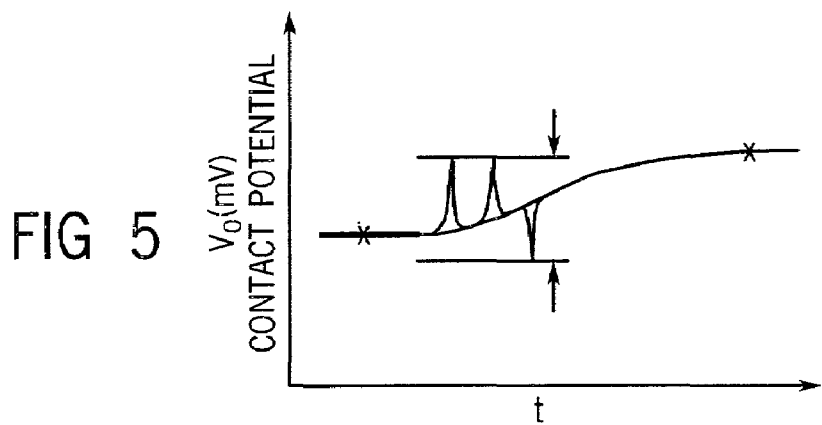
FIG. 5 illustrates a schematic plot of contact potential of oil measured by the sensor of FIG. 1 as a function of time of oil use.

FIG. 3 illustrates schematically the sensor 10 wherein oil 46, containing molecules 45, flow past the two materials 20 and 30 positioned within a pipe 50. FIGS. 3 and 4 illustrate conceptually the separation of the oil molecules 45 which impinge on walls 60 and 65 of the materials 20 and 30, respectively. A resulting contact potential V will then develop and is shown schematically in FIG. 5 as a function of time of oil use. The plot can yield signatures associated with the chemical or dielectric state of the oil 46. Chemical changes can include degradation of the molecular makeup of the oil 46 and contamination by other materials in contact with the oil 46. In the most general sense the sensor 10 can monitor any fluid or gas stream which yields an adequate contact potential for examination and analysis by a user.

Figure 6:
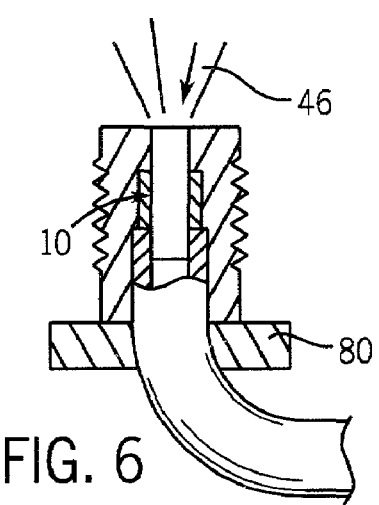
FIG. 6 illustrates an example use of the contact potential difference sensor in an oil drain plug environment.

A specific commercial illustration of the use of the sensor 10 is shown in FIG. 6. A section of an oil pan 70 includes a drain plug 80 in an automotive oil system. As the oil 46 moves in the vicinity of the sensor 10 and the dielectric properties change, the sensor 10 indicates a change which is manifested by the contact potential being measured.

Figure 7A:
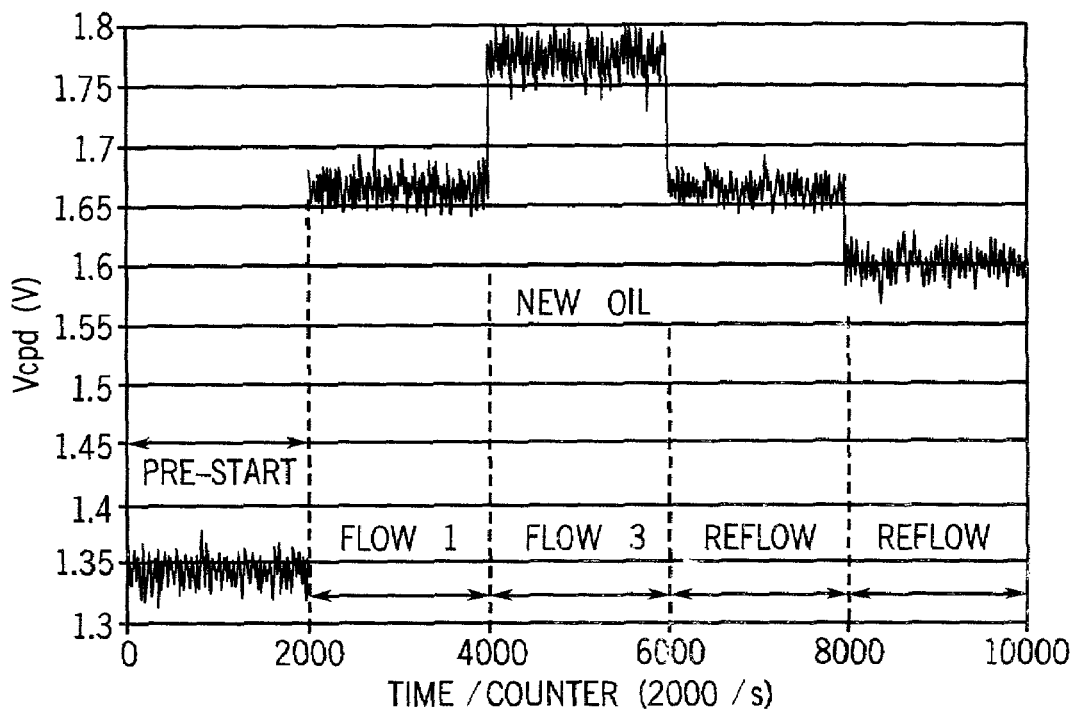
FIG. 7A illustrates contact potentials for selected time periods of unused oil flow through a system.
Figure 7B:
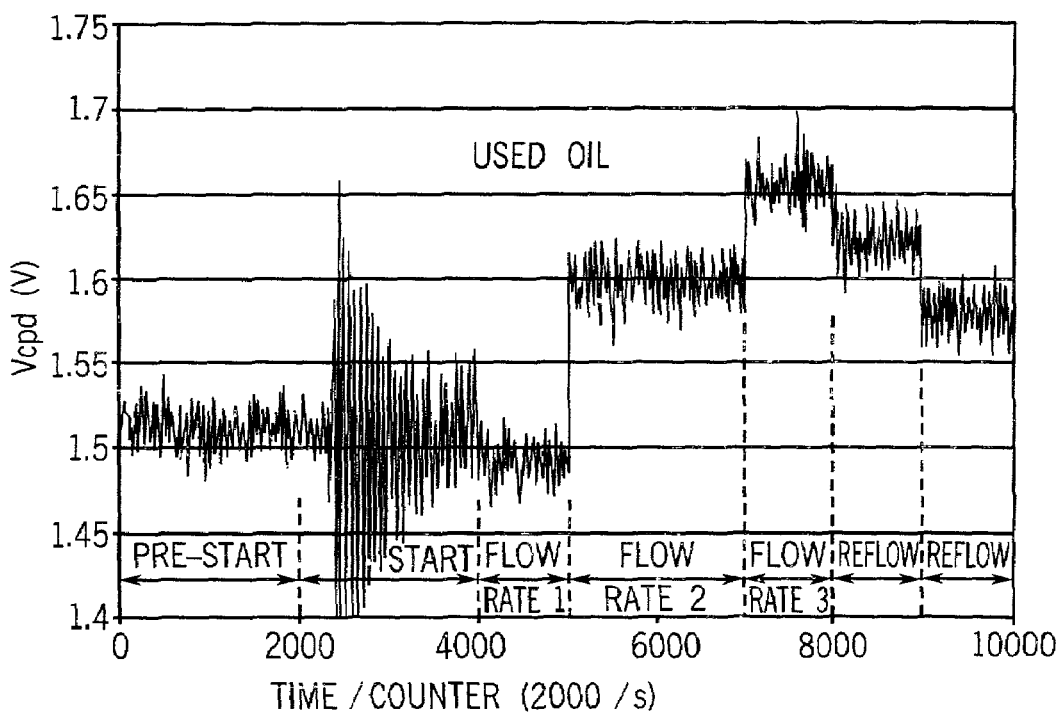
FIG. 7B illustrates contact potentials for a used oil undergoing flow through a system.

FIGS. 7A and 7B illustrate experimental operation of the sensor 10 shown in FIGS. 1–3. A conventional brand of new and used motor oil were monitored by the sensor 10, and the results are shown in FIGS. 7A and 7B, respectively. A variety of important dielectric changes can be characterized in this manner and clearly illustrates the usefulness of the sensor 10 in monitoring a fluid, such as an oil, or other such characterizable material.

The illustrated sensor 10 has applications in any system having open or closed loops wherein a fluid can be passed by the sensor 10 enabling characterization of the dielectric properties of the fluid. Examples include, without limitation, automotive systems, chemical plants, selected high pressure gaseous environments, such as turbine environments, and environmental monitors.

These and other objects, advantages and features of the invention together with the organization and manner of operation thereof will become apparent from the following detailed description when taken into conjunction with the accompanying drawings wherein like elements have like numerals throughout the drawings.

What is claimed is:

1. A method of monitoring chemical changes of a fluid, comprising the steps of:
   providing a contact potential difference sensor;
   flowing a fluid past the sensor to generate a contact potential; and
   characterizing the contact potential as a measure of chemical changes of the fluid.

2. The method as defined in claim 1 wherein the fluid comprises an oil.

3. The method as defined in claim 1 wherein the characterizing step includes measuring the contact potential of a standard fluid and comparing with the contact potential of a test fluid.

4. The method as defined in claim 3 wherein the step of measuring the contact potential of a standard fluid includes establishing chemical signatures associated with a particular chemical change of the fluid.

5. The method as defined in claim 4 wherein the chemical change is selected from the group consisting of a molecular change relative to the standard fluid and presence of a contaminating material.

6. The method as defined in claim 5 wherein the molecular change is selected from the group consisting of thermally induced chemical degeneration and chemical reaction with a contaminant.

7. The method as defined in claim 1 wherein the fluid is selected from the group consisting of condensed matter and gaseous matter.

8. The method as defined in claim 1 further including the step of outputting an alarm indication upon detecting the chemical changes being outside an acceptable range.

9. The method as defined in claim 8 further including a display for use by an operator to view the alarm indication.

10. A system for monitoring operational chemical changes of a fluid, comprising:
    a contact potential sensor;
    a fluid disposed in a closed loop; and
    an output device to indicate the operational chemical changes of the fluid.

11. The system as defined in claim 10 wherein the fluid comprises a hydrocarbon fluid.

12. The system as defined in claim 11 wherein the hydrocarbon fluid comprises an oil.

13. The system as defined in claim 10 wherein the output device comprises a machine maintenance indicator component.

14. The system as defined in claim 10 further including a computer for analyzing the operational chemical changes of the fluid.

15. The system as defined in claim 10 wherein the computer includes data characteristic of a plurality of particular degraded operational chemical changes of the fluid.

16. The system as defined in claim 15 wherein the data characteristic of particular degraded state for the operational chemical changes is selected from the group consisting of chemically changed fluid relative to a starting virgin fluid, fluid chemically reacted with an environmental material and contaminating extrinsic material.

17. The system as defined in claim 10 further including an oil pan of an engine having a drain plug wherein the sensor is disposed near the drain plug.

18. The system as defined in claim 10 further including a closed loop which contains the fluid, the closed loop part of an industrial unit.

19. The system as defined in claim 18 wherein the industrial unit is selected from the group consisting of a chemical plant, an environmental apparatus, an internal combustion engine and a turbine.

20. The system as defined in claim 10 further including data storage containing data sets characteristic of desired chemical states of a fluid, whereby data from a fluid under test can be compared with the desired chemical state data.

* * * * *